(12) United States Patent
Chevalier

(10) Patent No.: US 6,906,106 B2
(45) Date of Patent: Jun. 14, 2005

(54) COMPOSITIONS FOR THE SKIN COMPRISING FIBERS AND UBIQUINONES AND METHODS OF USING THE SAME

(75) Inventor: Veronique Chevalier, Villecresnes (FR)

(73) Assignee: L'Oreal, Paris (FR)

( * ) Notice: Subject to any disclaimer, the term of this patent is extended or adjusted under 35 U.S.C. 154(b) by 44 days.

(21) Appl. No.: 10/102,632

(22) Filed: Mar. 22, 2002

(65) Prior Publication Data

US 2002/0197288 A1 Dec. 26, 2002

(30) Foreign Application Priority Data

Mar. 23, 2001 (FR) .............................. 01 03960

(51) Int. Cl.[7] .................. A01N 35/00; A61K 31/12
(52) U.S. Cl. .................. 514/690; 514/183; 514/412; 514/675; 514/54; 424/59; 424/62; 424/63; 424/64; 424/78.03; 424/94.1; 424/94.3
(58) Field of Search .................. 514/183, 412, 514/690; 424/59, 62, 63, 64, 78.03, 78.06, 401

(56) References Cited

U.S. PATENT DOCUMENTS

| 3,939,285 | A | * | 2/1976 | Garrett, Sr. et al. | |
|---|---|---|---|---|---|
| 5,378,461 | A | * | 1/1995 | Neigut | 424/94.1 |
| 5,889,062 | A | * | 3/1999 | Hoppe et al. | |
| 5,965,146 | A | * | 10/1999 | Franzke et al. | |
| 6,048,886 | A | * | 4/2000 | Neigut | 514/412 |
| 6,207,137 | B1 | * | 3/2001 | Shuch et al. | |
| 6,261,575 | B1 | * | 7/2001 | Hoppe et al. | |
| 6,306,407 | B1 | * | 10/2001 | Castro et al. | |
| 6,656,487 | B2 | * | 12/2003 | Afriat et al. | 424/401 |
| 6,689,835 | B2 | * | 2/2004 | Amarasekera et al. | 524/495 |

FOREIGN PATENT DOCUMENTS

| EP | 0 261 362 A2 | * | 3/1988 |
| EP | 1 053 742 A1 | | 11/2000 |
| EP | 1 064 930 A1 | | 1/2001 |
| EP | 1 172 078 A2 | | 1/2002 |

* cited by examiner

*Primary Examiner*—James O. Wilson
*Assistant Examiner*—Traviss C. McIntosh, III
(74) *Attorney, Agent, or Firm*—Oblon, Spivak, McClelland, Maier & Neustadt, P.C.

(57) ABSTRACT

The present invention relates to a composition for topical application on the skin, comprising fibers and at least one or two or more compounds selected from the group of the ubiquinones and derivatives thereof. The ubiquinone can in particular be coenzyme Q10. The composition of the invention makes it possible to improve the appearance of the skin, immediately as well as in the longer term, and to mask the imperfections and/or signs of ageing of the skin while maintaining a natural appearance of the skin.

60 Claims, No Drawings

COMPOSITIONS FOR THE SKIN COMPRISING FIBERS AND UBIQUINONES AND METHODS OF USING THE SAME

CROSS REFERENCES TO RELATED APPLICATIONS

This application claims priority to French Patent Application No. 0103960, filed on Mar. 23, 2001, which is incorporated herein by reference in its entirety.

BACKGROUND OF THE INVENTION

1. Field of the Invention

The present invention relates to compositions for topical application on the skin and to methods of using such compositions, particularly in the fields of cosmetology and dermatology.

2. Discussion of the Background

The use of ubiquinones in particular in cosmetic compositions, for example for treating the signs of ageing of the human skin, is known. For example, it is known that, in the course of the ageing process, various signs appear on the human skin which are highly characteristic of this ageing and which are manifested in particular in a modification of the structure and of the cutaneous function. The main clinical signs of skin ageing are in particular the following: the appearance of fine lines and then deep wrinkles which increases with age, and the disruption of the "grain" of the skin; that is, the microrelief is less uniform and exhibits an anisotropic character.

Furthermore, the complexion of the skin is generally modified; it appears paler and yellower, which appears to be due essentially to disruption of the microcirculation (less haemoglobin in the papillary dermis). A large number of colored spots appear on the surface, owing to impaired melanogenesis. Another clinical sign of ageing is the dry and rough appearance of the skin, which is due essentially to increased desquamation; by diffracting the rays of light, these squamae are also involved in the development of a slightly greyish appearance of the complexion.

Ubiquinones are therefore used to treat some of these signs of ageing. For example, ubiquinones are used to treat or prevent dryness of the skin, couperose, chronological ageing, the rough appearance of the skin, and to treat fine lines and wrinkles and/or skin blemishes.

Ubiquinones are additionally used to prevent regreasing of the skin and/or hair after washing, to provide nutrients to the skin and to prevent it from drying out, to treat acne, and to treat wounds.

However, these active compounds have the drawback of being effective only after a certain time of application. However, there is more and more a desire to obtain an immediate effect of the active compounds used, leading rapidly to smoothing of the lines and wrinkles, the disappearance of marks of tiredness from the skin, and the masking of the visible signs of ageing, so as to obtain a skin which is smooth and which glows with good health.

Thus, there remains a need for ubiquinone-containing compositions which do not suffer from the above-mentioned drawbacks.

SUMMARY OF THE INVENTION

Accordingly, it is one object of the present invention to provide novel ubiquinone-containing compositions which exhibit a quick or immediate effect on the skin.

It is another object of the present invention to provide novel methods of using such compositions.

These and other objects, which will become apparent during the following detailed description, have been achieved by the inventor's surprising discovery that the combination of fibers and an ubiquinone makes it possible to obtain both an immediate effect and a long-term effect on the visible signs of ageing (lines, wrinkles, blemishes, dull complexion) and any other imperfection of the keratinous matter treated, and especially the skin, while retaining the natural appearance of the skin. Furthermore, the fibers make it possible to provide good cosmetic properties, such as softness and comfort during application to the skin, and ease of application.

DETAILED DESCRIPTION OF THE PREFERRED EMBODIMENTS

Thus, in a first embodiment, the present invention provides compositions for topical application on the skin, comprising:

(a) fibers; and
(b) at least one or two or more compounds selected from the group consisting of the ubiquinones and derivatives thereof.

The term "topical application" as used herein refers to external application to the keratinous matter, and "keratinous matter" means, in particular, the skin, including the scalp, and the mucosae (lips). The composition may in particular be a cosmetic or dermatological composition for the skin and the lips.

Since the composition of the invention is intended for topical application it comprises a physiologically acceptable medium, i.e., a medium compatible with all keratinous matter, such as the skin of the face (forehead, cheeks, lip contour), hands and body, including the scalp, and lips.

The ubiquinones are quinone derivatives with or without isoprene side chains. They are described in the Merck Index, 11th Edition, Merck & Co., Inc. Rahway, N.Y., USA, Abstr. 9751 (1989), which is incorporated herein by reference. Those which contain an isoprene side chain are also referred to by the term coenzymes Q. In coenzymes Q, the number of isoprene units in the side chain is given by the number n which accompanies Q in the designation coenzyme Qn. Typically, n is an integer ranging from 0 to 12, in particular from 1 to 12, and more particularly from 6 to 10. The ubiquinone may also not contain an isoprene side chain, and may be selected from alkylubiquinones in which the alkyl group may contain from 1 to 20 and preferably from 1 to 12 carbon atoms, such as, for example, decylubiquinones such as 6-decylubiquinone or 2,3-dimethoxy-5-decyl-1,4-ubiquinone, derivatives thereof, and mixtures thereof.

According to one preferred embodiment of the present invention, the ubiquinone used in the composition of the invention is coenzyme Q10.

The composition of the invention may comprise one or more ubiquinones or ubiquinone derivatives described above from the same category or from different categories. The amount of ubiquinone(s) in the composition depends on the ubiquinone used and on the end use of the composition. The ubiquinone(s) must be present in an effective amount, i.e., an amount sufficient to obtain the desired aim, which is to improve the appearance of the skin and to treat the skin. This amount may range, for example, from 0.0001 to 30% by weight, preferably from 0.01 to 20% by weight, more preferably from 0.1 to 15% by weight and better still from 0.5 to 10% by weight, of active compound relative to the total weight of the composition.

The fibers which can be used in the composition of the present invention may be hydrophilic or hydrophobic fibers of synthetic or natural origin, organic or inorganic.

These fibers may be short or long and single or organized, for example twisted. They may have any shape or morphology and in particular may have a circular or polygonal (square, hexagonal or octagonal) cross section depending on the specific application envisaged. In particular, their ends are typically blunted and/or smoothed in order to prevent wounding.

In particular, the fibers may have a length (L) ranging from 1 $\mu$m (0.001 mm) to 10 mm, preferably from 0.1 $\mu$m to 5 mm, and more preferably from 0.1 mm to 1.5 mm. Their cross section is small enough such that the fiber may be contained within a circle of diameter (D) ranging from 1 nm (0.001 $\mu$m) to 100 $\mu$m, preferably ranging from 1 nm (0.001 $\mu$m) to 50 $\mu$m, and more preferably from 5 $\mu$m to 40 $\mu$m.

The fibers used in accordance with the present invention preferably have a shape factor (aspect ratio), i.e., an L/D (length/diameter) ratio, ranging from 3.5 to 2,500, more preferably from 5 to 500 and better still from 5 to 150.

The linear density of the fibers is often given in denier or decitex. The denier is the weight in grams per 9 km of yarn. Preferably, the fibers used in accordance with the present invention have a linear density ranging from 0.15 to 30 deniers, more preferably from 0.18 to 18 deniers.

The shape factor, linear density, and morphology of the fibers are the three factors which are important for defining a fiber, in the context of the present invention.

The fibers may be those used in the manufacture of textiles and, in particular, fibers of silk, cotton, wool, linen, cellulose extracted in particular from wood, vegetables or algae, polyamide (Nylon® ), modified cellulose (rayon, viscose, acetate, especially rayon acetate), poly-p-phenyleneterephthalamide, especially Kevlar®, acrylic fibers, particularly those of polymethyl methacrylate or of poly-2-hydroxyethyl methacrylate, fibers of polyolefin and in particular of polyethylene or polypropylene, glass, silica, aramid, carbon, especially in the form of graphite, poly (tetrafluoroethylene) (Teflon®), insoluble collagen, polyesters, polyvinyl chloride or polyvinylidene chloride, polyvinyl alcohol, polyacrylonitrile, chitosan, polyurethane or polyethylene phthalate, and fibers formed from a blend of polymers such as those mentioned above, such as polyamide/polyester fibers.

Examples of polyurethane fibers which may be mentioned are poly(urethane-urea) polymer fibers, belonging to the elastane class, and especially those sold under the name Lycra® by the company DuPont.

It is also possible to use the absorbable synthetic fibers used in surgery, such as fibers prepared from glycolic acid and caprolactone (Monocryl from Johnson & Johnson); absorbable synthetic fibers of the lactic acid-glycolic acid copolymer type (Vicryl from Johnson & Johnson); polyester terephthalatic fibers (Ethibond from Johnson & Johnson) and stainless steel filaments (Acier from Johnson & Johnson).

It is also possible to use mixtures of the abovementioned fibers.

Furthermore, the fibers may or may not have a surface treatment and may or may not be coated. They may especially be coated and/or functionalized fibers, the term "functionalized" meaning that the fibers are surface-treated so as to modify their properties.

As coated fibers which can be used in the invention mention may be made of polyamide fibers coated with copper sulfide for an antistatic effect (for example R-STAT from Rhodia) or another polymer which allows a specific organization of the fibers (treatment of specific surface) or a surface treatment inducing color/hologram effects (Lurex fiber from Sildorex, for example).

The fibers can also be functionalized, that is to say modified so as to have a specific function. This functionalization of the fibers can be carried out both on the fibers and in the fibers and by any method which makes it possible to attach a compound to the fibers or to trap it within the cavities formed by the geometry of the fibers. Mention may be made, as methods, of, for example, coating the fibers with an active principle; fixing, to the fibers, particles enclosing an active principle, such as nanocapsules or nanospheres; adsorption in the fibers; or fixing by chemical reaction. It is thus possible to use fibers having specific functional purposes, for example fibers which are stabilized against UV radiation by modification with chemical or physical sunscreens; fibers which have been rendered bactericidal or antiseptic by modification with preservatives or antibacterials; fibers which have been colored by modification with coloring molecules; fibers which have been rendered keratolytic or desquamating by modification with keratolytic or desquamating agents; fibers which have been rendered hydrating by modification with hydrating agents or water-retaining polymers; fibers which have been rendered fragrant by modification with a fragrance; fibers which have been rendered analgesic or soothing by modification with an antiinflammatory or a soothing agent; or fibers which have been rendered resistant to perspiration by modification with an antiperspirant Depending on their properties, the fibers used in accordance with the present invention may be introduced in an aqueous medium, in an oily medium or in a powder.

The fibers which can be used in accordance with the present invention are preferably selected from polyamide fibers, poly-p-phenyleneterephthalamide fibers, cotton fibers, and mixtures thereof. Their length may range from 0.1 to 10 mm, preferably from 0.1 to 1 mm; their average diameter may range from 5 to 50 $\mu$m; and the shape factor ranges preferably from 5 to 150.

In particular it is possible to use the polyamide fibers sold by Etablissements P. Bonte under the name Polyamide 0.9 dtex 0.3 mm, having an average diameter of from 15 to 20 $\mu$m, a linear density of approximately 0.9 dtex (0.81 denier) and a length ranging from 0.3 mm to 1.5 mm. It is also possible to use poly-p-phenylene-terephthalamide fibers having an average diameter of 12 $\mu$m and a length of approximately 1.5 mm, such as those sold under the name Kevlar Floc by Du Pont Fibers. These polyamide fibers are preferably introduced in an oily medium or by a dry route in a powder.

It is also possible to use cotton fibers, for example those having a mean diameter of 20 $\mu$m, a length of 0.3 mm, and a shape factor of 15, such as those sold by the company Filature de Lomme, by the company Textiles des Dunes, the Institut Textile de France, or by the company Velifil.

The fibers may be present in the composition of the present invention in an amount ranging for example from 0.01 to 50% by weight, preferably from 1 to 20% by weight, more preferably from 5 to 10% by weight, of active compound, relative to the total weight of the composition.

The physiologically acceptable medium of the compositions for topical application, according to the present invention, may more particularly comprise water and optionally a physiologically acceptable organic solvent selected, for example, from lower alcohols containing 1 to 8 carbon atoms and preferably 1 to 6 carbon atoms, such as ethanol, isopropanol, propanol and butanol; polyethylene glycols having from 6 to 80 ethylene oxide units; and polyols such as propylene glycol, isoprene glycol, butylene glycol, glycerol and sorbitol.

This medium may also be an anhydrous medium, especially an oily medium comprising oils and/or fatty substances other than oils.

According to one preferred embodiment of the present invention, the medium of the composition comprises water. This aqueous medium preferably has a pH which is compatible with the skin, ranging preferably from 3 to 8 and more preferably from 4.5 to 7.

When the composition comprises an aqueous or aqueous-alcoholic medium, it is possible to add a fatty phase (or oily phase) to this medium in order to make the compositions of the present invention softer and more nourishing.

The oily phase commonly contains at least one oil. As oils which can be used in the composition of the present invention, mention may be made, for example, of:

hydrocarbon oils of animal origin, such as perhydrosqualene;

hydrocarbon oils of plant origin, such as the liquid triglycerides of fatty acids containing 4 to 10 carbon atoms such as the triglycerides of heptanoic or octanoic acids or else, for example, sunflower oil, corn oil, soybean oil, marrow oil, grapeseed oil, sesame oil, hazelnut oil, apricot oil, macadamia oil, sandarac oil, castor oil, avocado oil, caprylic/capric acid triglycerides such as those sold by Stearineries Dubois or those sold under the names Miglyol 810, 812, and 818 by Dynamit Nobel, jojoba oil, and karite butter;

synthetic esters and ethers, especially those of fatty acids, such as the oils of formulae $R^1COOR^2$ and $R^1OR^2$ in which $R^1$ represents the residue of a fatty acid containing 8 to 29 carbon atoms and $R^2$ represents a branched or unbranched hydrocarbon chain containing 3 to 30 carbon atoms, such as, for example, purcellin oil, isononyl isononanoate, isopropyl myristate, 2-ethylhexyl palmitate, 2-octyldodecyl stearate, 2-octyldodecyl erucate, and isostearyl isostearate; hydroxylated esters such as isostearyl lactate, octyl hydroxystearate, octyldodecyl hydroxystearate, diisostearyl malate, triisocetyl citrate, and the heptanoates, octanoates and decanoates of fatty alcohols; polyol esters, such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or nonvolatile liquid paraffins and derivatives thereof, vaseline, polydecenes, and hydrogenated polyisobutene such as Parleam® oil;

fatty alcohols having 8 to 26 carbon atoms, such as cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;

alkylated fatty alcohols and especially ethoxylated fatty alcohols such as oleth-12;

partially hydrocarbon-based and/or silicon-based fluoro oils such as those described in the document JP-A-2-295912, which is incorporated herein by reference. As fluoro oils mention may also be made of perfluoromethylcyclopentane and perfluoro-1,3-dimethylcyclohexane, sold under the names FLUTEC PC1® and FLUTEC PC3® by the company BNFL Fluorochemicals; perfluoro-1,2-dimethylcyclobutane; perfluoroalkanes such as dodecafluoropentane and tetradecafluorohexane, sold under the names PF 5050® and PF 5060® by the 3M Company, or else the bromoperfluorooctyl sold under the name FORALKYL® by Atochem; nonafluoromethoxybutane sold under the name MSX 4518® by the 3M Company, and nonafluoroethoxyisobutane; perfluoromorpholine derivatives, such as 4-trifluoromethylperfluoromorpholine sold under the name PF 5052® by the 3M Company;

silicone oils such as volatile or nonvolatile polydimethylsiloxanes (PDMS) which have a linear or cyclic silicone chain and are liquid or pastelike at ambient temperature, especially cyclopolydimethylsiloxanes (cyclomethicones) such as cyclohexasiloxane; polydimethylsiloxanes containing alkyl, alkoxy or phenyl groups, pendant or at the end of the silicone chain, these groups having from 2 to 24 carbon atoms; phenylated silicones such as phenyltrimethicones, phenyldimethicones, phenyltrimethylsiloxydiphenylsiloxanes, diphenyldimethicones, diphenylmethyldiphenyltrisiloxanes, 2-phenylethyl trimethylsiloxysilicates, and polymethylphenylsiloxanes; and mixtures thereof.

A hydrocarbon oil in the list of oils mentioned above is any oil containing primarily carbon and hydrogen atoms and optionally ester, ether, fluoro, carboxylic acid and/or alcohol groups.

The other fatty substances which may be present in the oily phase are, for example, fatty acids containing 8 to 30 carbon atoms, such as stearic acid, lauric acid, palmitic acid and oleic acid; waxes such as lanolin, beeswax, carnauba wax or candelilla wax, paraffin waxes, lignite waxes or microcrystalline waxes, ceresine or ozokerite, synthetic waxes such as polyethylene waxes and Fischer-Tropsch waxes; gums such as silicone gums (dimethiconol); silicone resins such as trifluoromethyl-$C_{1-4}$-alkyldimethicone and trifluoropropyldimethicone; and silicone elastomers such as the products sold under the names KSG by Shin-Etsu, under the names Trefil, BY29, or EPSX by Dow Corning or under the names Gransil by Grant Industries.

These fatty substances may be selected by the person skilled in the art in order to prepare a composition having the desired properties, for example of consistency or texture.

The compositions of the present invention may be in any of the pharmacological forms which are conventionally used for topical application and particularly in the form of aqueous, aqueous-alcoholic or oily solutions, oil-in-water (O/W) or water-in-oil (W/O) emulsions or multiple (W/O/W or O/W/O) emulsions, aqueous or oily gels, liquid, pastelike or solid anhydrous products, or dispersions of a fatty phase in an aqueous phase with the aid of spherules, it being possible for these spherules to be polymeric nanoparticles such a nanospheres and nanocapsules, or lipid vesicles of ionic and/or nonionic type. These compositions are prepared in accordance with the usual methods.

Furthermore, the compositions used in accordance with the present invention may be more or less fluid and may have the appearance of a white or coloured cream, an ointment, a milk, a lotion, a serum, a paste, or a foam. They may, where appropriate, be applied to the skin in the form of an aerosol. They may also be in solid form, for example in the form of a stick.

According to one particular embodiment of the present invention, the composition of the invention is an emulsion.

The proportion of the oily phase of the emulsion may range from 5 to 80% by weight, and preferably from 5 to 50% by weight, relative to the total weight of the composition. The oils, the emulsifiers, and the coemulsifiers used in the composition in emulsion form are selected from those which are conventionally used in the field of cosmetology or dermatology. The emulsifier and coemulsifier are generally present in the composition in a proportion ranging from 0.3 to 30% by weight, preferably from 0.5 to 20% by weight, relative to the total weight of the composition. The emulsion may further comprise lipid vesicles.

The emulsions generally comprise at least one emulsifier selected from amphoteric, anionic, cationic, and nonionic emulsifiers, which are used individually or as a mixture. The emulsifiers are selected appropriately depending on the emulsion to be obtained (W/O or O/W). When the emulsion is a multiple emulsion, it generally comprises a surfactant in the primary emulsion and a surfactant in the external phase into which the primary emulsion is introduced.

As emulsifying surfactants which can be used for the preparation of the O/W emulsions mention may be made, for example, of the alkyl esters or ethers of sorbitan, of glycerol or of sugars; silicone surfactants such as dimethicone copolyols, for instance the polyglyceryl-4 isostearate/cetyl dimethicone copolyol/hexyl laurate mixture sold under the name Abil WE 09 by Goldschmidt, the mixture of cyclomethicone and dimethicone copolyol sold under the names DC 5225 C and DC 3225 C by Dow Corning, and the alkyldimethicone copolyols such as laurylmethicone copolyol sold under the name Dow Corning 5200 Formulation Aid by Dow Corning and the cetyl dimethicone copolyol sold under the name Abil EM 90® by Goldschmidt.

As emulsifiers for the O/W emulsions mention may be made, for example, of nonionic emulsifiers such as the alkoxylated (more particularly polyethoxylated) esters of fatty acids and glycerol; alkoxylated esters of fatty acids and sorbitan; alkoxylated (ethoxylated and/or propoxylated) esters of fatty acids; alkoxylated (ethoxylated and/or propoxylated) ethers of fatty alcohols; sugar esters such as sucrose stearate, and mixtures thereof, such as, for example, the mixture of glyceryl stearate and PEG-100 stearate which is sold under the name Arlacel 165 by Uniqema.

It is also possible to prepare emulsions without surfactants by using appropriate compounds, for example polymers having emulsifying properties such as Carbopol 1342 and Pemulen, and particles of ionic or nonionic polymers, more particularly anionic polymer particles such as, in particular, polymers of isophthalic acid or sulphoisophthalic acid, and especially the phthalate/sulphoisophthalate/glycol copolymers (for example diethylene glycol/phthalate/isophthalate/ 1,4-cyclohexanedimethanol; CTFA name: diglycol/CHDM/ isophthalates/SIP copolymer) sold under the names Eastman AQ polymer (AQ35S, AQ38S, AQ55S, AQ48 Ultra) by Eastman Chemical.

The cosmetic or dermatological composition of the present invention may further comprise conventional adjuvants which are common in the field of cosmetology or dermatology, such as hydrophilic or lipophilic gelling agents, active hydrophilic or lipophilic agents other than those mentioned above, preservatives, antioxidants, solvents, perfumes, fillers, bactericides, odor absorbers, colorants, salts, polymers (for example acrylates/ dimethicone copolymer sold under the name KP-561 by Shin-Etsu, as a dispersant). The amounts of these various adjuvants are those which are commonly used in the field under consideration, and are for example from 0.01 to 20% by weight of the total weight of the composition. Depending on their nature, these adjuvants may be introduced into the fatty phase, into the aqueous phase, and/or into the lipid spherules.

The compositions of the present invention may in particular comprise one or more active lipophilic or hydrophilic substances other the ubiquinones, selected from moisturizers, free-radical scavengers, keratolytic agents, vitamins, antielastase and anticollagenase agents, proteins, fatty acid derivatives, steroids, trace elements, whiteners, algal extracts, plankton extracts, filters, enzymes, flavonoids, ceramides, and mixtures thereof.

As moisturizers, mention may be made in particular of sodium lactate; polyols, and especially glycerol, sorbitol and polyethylene glycols; mannitol, amino acids; hyaluronic acid; lanolin; urea and mixtures containing urea, such as NMF (natural moisturizing factor); vaseline; and mixtures thereof.

As keratolytic agents, mention may be made, for example, of α-hydroxy acids, particularly the acids derived from fruit, such as glycolic, lactic, malic, citric, tartaric, and mandelic acids and their derivatives; β-hydroxy acids such as salicylic acid and its derivatives such as 5-n-octanoylsalicylic acid or 5-n-dodecanoylsalicylic acid; (α-keto acids such as ascorbic acid or vitamin C and its derivatives; β-keto acids; retinoids such as retinol (vitamin A) and its esters, retinal, retinoic acid and its derivatives, those described in the documents FR-A-2 570 377, EP-A-199 636, EP-A-325 540 and EP-A-402 072 (all of which are incorporated herein by reference), and mixtures thereof.

As vitamins, besides the vitamins A, E, and C indicated above, mention may be made in particular of vitamin B3 (or vitamin PP or niacinamide), vitamin B5 (panthenol), the derivatives and precursors of these vitamins, and those of the vitamins A, E, and C, such as lycopenes or carotenes which are precursors of vitamin A, and mixtures thereof.

As free-radical scavengers, mention may be made in particular of phosphonic acid derivatives; ethylenediaminetetraacetic acid and its salts such as the sodium salt; guanosine; superoxydismutase; tocopherol (vitamin E) and its derivatives (acetate); ethoxyquin; lactoferrin; lactoperoxidase, and the nitroxide derivatives; superoxide dismutases; glutathione peroxidase; plant extracts with antiradical activity such as the aqueous wheatgerm extract sold by Silab under the reference Detoxiline; and mixtures thereof.

As antielastase agents, mention may be made in particular of peptide derivatives, and especially the peptides from seeds of leguminous plants such as those sold by Laboratoires Seriobiologiques de Nancy under name Parelastyl; the N-acylaminoamide derivatives described in French Patent Application FR0007344 (which is incorporated herein by reference), such as, for example, ethyl {2-[acetyl(3-trifluoromethylphenyl)amino]-3-methylbutyrylamino}acetate and {2-[acetyl(3-trifluoromethylphenyl)amino]-3-methylbutyrylamino}acetic acid and mixtures thereof. As anticollagenase agents, mention may be made of metalloprotease inhibitors, such as ethylenediaminetetraacetic acid (EDTA) and cysteine; and mixtures thereof.

As proteins, mention may be made for example of wheat or soya proteins, their hydrolysates, such as those sold by Silab under the reference Tensine, and mixtures thereof.

As fatty acid derivatives, mention may be made in particular of polyunsaturated phospholipids including essential fatty acid phospholipids from pulp, and mixtures thereof.

As steroids, mention may be made, for example, of DHEA or dehydroepiandrosterone, its biological precursors, its metabolites, and mixtures thereof. By biological precursors of DHEA are meant in particular Δ5-pregnenolone, 17α-hydroxypregnenolone and 17α-hydroxypregnenolone sulphate. By derivatives of DHEA are meant both its metabolic derivatives and its chemical derivatives. As metabolic derivatives mention may be made in particular of Δ5-androstene-3,17-diol and especially 5-androstene-3β,17β-diol, Δ4-androstene-3,17-dione, 7-hydroxy-DHEA (7α-hydroxy-DHEA or 7β-hydroxy-DHEA) and 7-keto-DHEA, which is itself a metabolite of 7β-hydroxy-DHEA.

As trace elements, mention may be made, for example, of copper, zinc, selenium, iron, magnesium manganese, and mixtures thereof.

As whiteners, use may be made of any compound which allows the treatment or prevention of ageing blemishes, i.e. any depigmenting compound which acts directly on the vitality of the epidermal melanocytes in which melanogenesis takes place and/or which interferes with one of the steps in the biosynthesis of melanin, either by inhibiting one of the enzymes involved in melanogenesis or by inserting itself as a structural analogue of one of the chemical compounds in the melanin synthesis chain, and is therefore able to block the chain and ensure depigmentation. As active whiteners mention may be made, for example, of kojic acid and its derivatives, hydroquinone and its derivatives such as arbutin and its esters; ellagic acid and its derivatives; plant extracts, and especially extracts of liquorice, of mulberry or of skullcap; glutathione and its precursors; cysteine and its precursors; the aminophenol derivative compounds described in the document WO-A-99/10318 (which is incorporated herein by reference), such as, in particular, N-ethyloxycarbonyl-4-aminophenol, N-ethyloxycarbonyl-O-ethyloxycarbonyl-4-aminophenol, N-cholesteryloxycarbonyl-4-aminophenol, and N-ethylaminocarbonyl-4-aminophenol; and the mixtures of these compounds.

As algal extracts, mention may be made of extracts of red or brown algae, and for example the extract of brown algae from the class of the Laminaria, such as the extracts of the species *Laminaria digitata*, and more particularly that sold by CODIF under the name PHYCOSACCHARIDES, which is a concentrated solution of an oligosaccharide obtained by controlled enzymatic depolymerization of membrane polysaccharides from a brown algae. It comprises the catonated arrangement of two uric acids: mannuronic acid and guluronic acid.

As plankton extracts, mention may be made of the plankton in aqueous dispersion (CTFA name: Vitreoscilla Ferment) sold under the name MEXORYL SAH by Chimex.

As filters, use may be made, in the composition used in accordance with the present invention, of any of the chemical UVA and UVB sunscreens or physical filters which can commonly be used in the field of cosmetology.

As UVB filters, mention may be made, for example of:
(1) salicylic acid derivatives, especially homomenthyl salicylate and octyl salicylate;
(2) cinnamic acid derivatives, especially 2-ethylhexyl p-methoxycinnamate, sold by Givaudan under the name Parsol MCX;
(3) liquid β,β'-diphenylacrylate derivatives, especially 2-ethylhexyl α-cyano-α,β'-diphenylacrylate or octocrylene, sold by BASF under the name UVINUL N539;
(4) p-aminobenzoic acid derivatives;
(5) 4-methylbenzylidenecamphor, sold by Merck under the name EUSOLEX 6300;
(6) 2-phenylbenzimidazole-5-sulphonic acid, sold under the name EUSOLEX 232 by Merck;
(7) 1,3,5-triazine derivatives, especially:
2,4,6-tris[p-(2'-ethylhexyl-1'-oxycarbonyl)anilino]-1,3,5-triazine sold by BASF under the name UVINUL T150, and
dioctylbutamidotriazone, sold by Sigma 3V under the name UVASORB HEB; and
(8) the mixtures of these filters.

As UVA filters, mention may be made, for example, of:
(1) dibenzoylmethane derivatives, especially 4-(tert-butyl)-4'-methoxydibenzoylmethane, sold by Givaudan under the name PARSOL 1789;
(2) benzene-1,4-[di(3-methylidenecamphor-10-sulphonic)] acid optionally in partly or totally neutralized form, sold under the name MEXORYL SX by Chimex;
(3) benzophenone derivatives, for example:
2,4-dihydroxybenzophenone (benzophenone-1);
2,2',4,4'-tetrahydroxybenzophenone (benzopzhenone-2);
2-hydroxy-4-methoxybenzophenone (benzophenone-3), sold under the name UVINUL M40 by BASF;
2-hydroxy-4-methoxybenzophenone-5-sulphonic acid (benzophenone-4) and its sulfonate form (benzophenone-5), sold by BASF under the name UVINUL MS40;
2,2'-dihydroxy-4,4'-dimethoxybenzophenone (benzophenone-6);
5-chloro-2-hydroxybenzophenone (benzophenone-7);
2,2'-dihydroxy-4-methoxybenzophenone (benzophenone-8);
the disodium salt of 2,2'-dihydroxy-4,4'-dimethoxybenzophenone-5,5'-disulphonic acid (benzophenone-9);
2-hydroxy-4-methoxy-4'-methylbenzophenone (benzophenone-10);
benzophenone-11; and
2-hydroxy-4-(octyloxy)benzophenone (benzophenone-12);
(4) silane derivatives or polyorganosiloxanes containing a benzophenone group;
(5) anthranilates, especially menthyl anthranilate sold by Haarmann & Reimer under the name NEO HELIOPAN MA;
(6) compounds containing per molecule at least two benzoxazolyl groups or at least one benzodiazolyl group, especially 1,4-bisbenzimidazolylphenylene-3,3',5,5'-tetrasulphonic acid and its salts, which are sold by Haarmann & Reimer;
(7) silicon-containing derivatives of N-substituted benzimidazolylbenzazoles or of benzofuranylbenzazoles, and especially:
2-[1-[3-[1,3,3,3-tetramethyl-1-[(trimethylsilyl)oxy] disiloxanyl]propyl]-1H-benzimidazol-2-yl] benzoxazole;
2-[1-[3-[1,3,3,3-tetramethyl-1-[(trimethylsilyl)oxy] disiloxanyl]propyl]-1H-benzimidazol-2-yl] benzothiazole;
2-[1-(3-trimethylsilanylpropyl)-1H-benzimidazol-2-yl] benzoxazole;
6-methoxy-1,1'-bis(3-trimethylsilanylpropyl)-1H,1'H-[2,2']bibenzimidazolylbenzoxazole; and
2-[1-(3-trimethylsilanylpropyl)-1H-benzimidazol-2-yl] benzothiazole; which are described in the patent application EP-A-1 028 120 (which is incorporated herein by reference);

(8) triazine derivatives, and especially 2,4-bis{[4-(2-ethylhexyloxy)-2-hydroxy]phenyl}-6-(4-methoxyphenyl)-1,3,5-triazine, sold by Ciba Geigy under the name TINOSORB S, and 2,2'-methylenebis-[6-(2H-benzotriazol-2-yl)-4-(1,1,3,3-tetramethylbutyl) phenol] sold by Ciba Geigy under the name TINOSORB M; and (9) mixtures thereof.

It is also possible to use a mixture of two or more of these filters and a mixture of UVB filters and UVA filters, and also mixtures with physical filters.

As physical filters, mention may be made of titanium oxides (titanium dioxide, amorphous or crystalline in rutile and/or anatase form), zinc oxides, iron oxides, zirconium oxides, cerium oxides or mixtures thereof. These metal oxides may be in the form of particles having a micrometric or nanometric size (nanopigments). When in the form of nanopigments, the average particle sizes range for example from 5 to 100 nm. It is preferred to use nanopigments.

As enzymes, use may be made of any enzyme of animal, microbiological (bacterial, fungal or viral), or synthetic origin (obtained by chemical or biotechnological synthesis), in pure crystalline form or in diluted form in an inert diluent. Mention may be made, for example, of enzymes selected from among the lipases, proteases, phospholipases, cellulases, peroxidases, especially lactoperoxidases, catalases, superoxide dismutases, or from among plant extracts containing the aforementioned enzymes, and mixtures thereof.

As flavonoids mention may be made, for example, of isoflavonoids, which constitute a subclass of the flavonoids, formed of a 3-phenylchroman skeleton which can comprise various constituents and different levels of oxidation. The term "isoflavonoid" refers respectively to a number of classes of compound, among which mention may be made of isoflavones, isoflavanones, rotenoids, pterocarpans, isoflavans, isoflavan-3-enes, 3-arylcoumarins, 3-aryl-4-hydroxycoumarins, coumestans, coumaronochromones, α-methyldeoxybenzoins, 2-arylbenzofurans, and mixtures thereof. For a complete review of the isoflavonoids, the methods of analysing them, and their sources, reference may be made advantageously to chapter 5, "Isoflavonoids", written by P. M. Dewick, in The Flavonoids, published by Harbone, pp. 125–157 (1988), which is incorporated herein by reference.

The isoflavonoids may be of natural or synthetic origin. By "natural origin" is meant an isoflavonoid in the pure state or as a solution at various concentrations, obtained by various processes of extraction from an element, generally a plant, of natural origin. By "synthetic origin" is meant an isoflavonoid in pure form or as a solution at various concentrations, obtained by chemical synthesis.

It is preferred to use isoflavonoids of natural origin. Among these, mention may be made of the following: daidzin, genistin, daidzein, formononetin, cuneatin, genistein, isoprunetin and prunetin, cajanin, orobol, pratensein, santal, junipegenin A, glycitein, afrormosin, retusin, tectorigenin, irisolidone, jamaicin, and also analogues and metabolites thereof.

As ceramides, mention may be made, for example, of N-oleoyldihydrosphingosine, N-stearoylphytosphingosine, N-α-hydroxybehenoyldihydrosphingosine, N-α-hydroxypalmitoyl-dihydrosphingosine, N-linoleoyldihydrosphingosine, N-palmitoyldihydrosphingosine, N-stearoyldihydrosphingosine, N-behenoyldihydrosphingosine, and mixtures thereof.

As gelling agents, mention may be made, for example, of carboxyvinyl polymers such as Carbopols (carbomers) and Pemulens (acrylate/$C_{10}$-$C_{30}$ alkyl acrylate copolymer); polyacrylamides such as, for example, the crosslinked copolymers sold under the names Sepigel 305 (CTFA name: polyacrylamide/C13–14 isoparaffin/Laureth 7) or Simulgel 600 (CTFA name: acrylamide/sodium acryloyldimethyltaurate copolymer/isohexadecane/polysorbate 80) by Seppic; polymers and copolymers of 2-acrylamido-2-methylpropanesulphonic acid, optionally crosslinked and/or neutralized, such as poly(2-acrylamido-2-methylpropanesulphonic acid) sold by Hoechst under the commercial name "Hostacerin AMPS" (CTFA name: ammonium polyacryldimethyltauramide); cellulose derivatives such as hydroxyethylcellulose; polysaccharides, and especially gums such as xanthan gum; and mixtures thereof.

The composition may optionally comprise fillers. As fillers which can be used in the composition of the present invention, mention may be made for example, besides the pigments, of silica powder; talc; polyamide particles, particularly those sold under the name ORGASOL by Atochem; polyethylene powders; microspheres based on acrylic copolymers, such as those of ethylene glycol dimethacrylate/lauryl methacrylate copolymer, sold by Dow Corning under the name POLYTRAP; expanded powders such as hollow microspheres, and especially the microspheres sold under the name EXPANCEL by Kemanord Plast or under the name MICROPEARL F 80 ED by Matsumoto; powders of natural organic materials such as corn starch, wheat starch, or rice starch, crosslinked or noncrosslinked, such as starch powders crosslinked by octenylsuccinic anhydride, sold under the name DRY-FLO by National Starch; silicone resin microbeads such as those sold under the name TOSPEARL by Toshiba Silicone; and mixtures thereof. These fillers may be present in amounts ranging from 0 to 20% by weight, and preferably from 1 to 10% by weight, relative to the total weight of the composition.

The composition of the present invention may constitute a skin care product (cream, lotion) and/or a skin make-up product (foundation, blusher). It may be used in particular for combating and/or preventing ageing of the skin, particularly by smoothing the fine lines and reducing the wrinkles, by lightening the complexion, lessening or even removing the pigmentary blemishes which appear over time, by protecting the skin from UV radiation, by providing nutrition to the skin, and by regenerating the cutaneous tissues. It may also be used for preventing regreasing of the skin.

The composition of the present invention may also serve for treating acne and for treating wounds by promoting healing.

Thus, in a second embodiment the present invention accordingly farther provides a method for the preferably cosmetic treatment of the skin with the aim of smoothing fine lines, reducing wrinkles, lightening the complexion, lessening pigmentary blemishes, countering the adverse effects of UV radiation and preventing regreasing of the skin, by applying an effective amount of the present composition to the skin of a subject in need thereof.

In another embodiment, the invention further provides a method for the dermatological treatment of the skin, such as for acne and wound healing, comprising applying an effective amount of the present composition to the skin of a subject in need thereof.

The invention further provides a method of treatment of the signs of ageing of the skin, comprising applying an effective amount of a composition as defined above to the skin.

Thus, the present invention also provides novel methods for caring for the skin, by applying an effective amount of a composition according to the present invention to the skin. Of course the amount of the composition applied and the schedule of applying the composition will depend on the exact effect desired to be achieved. However, the compositions are suitably applied to the skin in an amount of 0.1 to 20 mg/cm$^2$, preferably 0.3 to 10 mg/cm$^2$, more preferably 1 to 5 mg/cm$^2$ (these numbers being approximate). The amount is generally 1 or 2 mg/cm$^2$. The exact quantity will depend on the desired result. The composition may be applied to the skin, the lips, and/or the scalp in a regime which includes application of the composition weekly, every other day, daily, or twice daily. The application of the composition to the skin, the lips, and/or the scalp may be continued until the desired degree of improvement is achieved or continued indefinitely for preventative purposes.

Other features of the invention will become apparent in the course of the following descriptions of exemplary embodiments which are given for illustration of the invention and are not intended to be limiting thereof.

EXAMPLES

In the examples which follow, the names are chemical names or CTFA names (International Cosmetic Ingredient Dictionary and Handbook) as appropriate and the amounts are given in percentages by weight unless specified otherwise.

Example 1

Water-in-Oil Emulsion

| Phase A: | |
|---|---|
| Hydrogenated polyisobutene | 5.5% |
| Isostearyl neopentanoate | 3.5% |
| PEG-20 stearate | 1% |
| Glyceryl stearate and PEG-100 stearate (Arlacel 165) | 2% |
| Cetyl alcohol | 0.5% |
| Stearyl alcohol | 0.5% |
| Stearic acid | 1% |
| Phase A': | |
| Cyclomethicone | 11% |
| Cotton fibers | 3% |
| Phase B: | |
| Preservatives | qs |
| Triethanolamine | 0.03% |
| Coenzyme Q10 | 0.05% |
| Water | qs 100% |
| Phase C: | |
| SEPIGEL 305 | 1% |

Procedure: Phase A is heated with stirring until homogeneous. After cooling, phase A' is added. Phase B is heated with stirring, and then B is poured into the mixture of phase A and phase A', still with stirring. After cooling to 50° C., phase C is incorporated into the emulsion.

A cream is obtained which is suitable for masking and treating wrinkles and fine lines of the skin.

Example 2

O/W Emulsion Without Surfactant

| Oily phase | |
|---|---|
| Vegetable oils | 12% |
| UVA filter | 2% |
| UVB filter | 4% |
| Cyclopentasiloxane | 6% |
| Aqueous phase | |
| Coenzyme Q10 | 0.01% |
| Disodium EDTA | 0.05% |
| Diglycol/CHDM/isophthalate/SIP copolymer (Eastman AQ38S from EASTMAN CHEMICAL) | 2% |
| Glycerol | 5% |
| Ethanol | 10% |
| Polyamide fibers | 2% |
| (Polyamide 0.9 dtex, 0.3 mm - from Paul Bonte) | 2% |
| Water qs | 100% |

Procedure: The oily phase and aqueous phase (without the fibers) are prepared separately, with heating, and the oily phase is poured into the aqueous phase with stirring, after which the fibers are added at 40° C.

A fluid emulsion is obtained which permits treatment of the signs of ageing of the skin at the surface and deep down.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A composition for topical application on the skin, comprising:

(a) fibers, wherein said fibers have a length (L) ranging from 1 μm to 10 mm; and (b) at least one ubiquinone.

2. The composition according to claim 1, wherein said fibers have a cross section contained within a circle of diameter (D) ranging from 1 nm to 100 μm.

3. The composition according to claim 1, wherein said fibers have a shape factor (L/D) ranging from 5 to 150.

4. The composition according to claim 1, wherein said fibers have a linear density ranging from 0.15 deniers to 30 deniers.

5. The composition according to claim 1, wherein said fibers are selected from the group consisting of fibers of silk, cotton, wool, linen, cellulose, polyamide, rayon, viscose, acetate, poly-p-phenyleneterephthalamide, acrylic fibers, fibers of polyolefin, glass, silica, aramid, carbon, poly(tetrafluoroethylene), insoluble collagen, polyesters, polyvinyl chloride, polyvinylidene chloride, polyvinyl alcohol, polyacrylonitrile, chitosan, polyurethane, polyethylene phthalate, fibers formed from a blend of polymers, absorbable synthetic fibers, and mixtures thereof.

6. The composition according to claim 1, wherein said fibers are coated or surface treated.

7. The composition according to claim 1, wherein said fibers are selected from the group consisting of polyamide fibers, poly-p-phenyleneterephthalamide fibers, cotton fibers, and mixtures thereof.

8. The composition according to claim 1, wherein said fibers are present in an amount ranging from 0.01% to 50% by weight, relative to the total weight of the composition.

9. The composition according to claim 1, wherein said fibers are present in an amount ranging from 1% to 20% by weight, relative to the total weight of the composition.

10. The composition according to claim 1, wherein said ubiquinone is selected from the group consisting of coenzymes Q, alkylubiquinones, and mixtures thereof.

11. The composition according to claim 1, wherein said ubiquinone is coenzyme Q10.

12. The composition according to claim 1, wherein said ubiquinone is present in an amount ranging from 0.0001% to 30% by weight, relative to the total weight of the composition.

13. The composition according to claim 1, wherein said ubiquinone is present in an amount ranging from 0.01% to 20% by weight, relative to the total weight of the composition.

14. The composition according to claim 1, further comprising at least one active substance selected from the group consisting of vitamins, moisturizers, free-radical scavengers, α-hydroxy acids, β-hydroxy acids, retinoids, antielastase agents, proteins, polyunsaturated phospholipids, steroids, trace elements, whiteners, algal extracts, planktons, sunscreens, enzymes, flavonoids, ceramides, and mixtures thereof.

15. The composition according to claim 1, further comprising a physiologically acceptable medium, wherein said physiologically acceptable medium comprises water.

16. The composition according to claim 1, which is in the form of an emulsion.

17. A method for the treatment of the skin, comprising applying the composition according to claim 1 to the skin, wherein said treatment of the skin is smoothing fine lines, reducing wrinkles, lightening the complexion, lessening pigmentary blemishes, protecting skin from UV radiation, or preventing regreasing of the skin.

18. A method of treatment of the signs of ageing of the skin, comprising applying an effective amount of a composition according to claim 1 to the skin of a subject in need thereof.

19. A method of treating acne or healing a wound to the skin, comprising applying an effective amount of a composition according to claim 1 to the skin of a subject in need thereof.

20. The composition according to claim 1, wherein said ubiquinone is water-soluble.

21. A composition for topical application on the skin, comprising:
    (a) fibers, wherein said fibers have a cross section contained within a circle of diameter (D) ranging from 1 nm to 100 1 μm; and
    (b) at least one ubiquinone.

22. A composition for topical application on the skin, comprising:
    (a) fibers, wherein said fibers have a shape factor (L/D) ranging from 5 to 150; and
    (b) at least one ubiquinone.

23. A composition for topical application on the skin, comprising:
    (a) fibers, wherein said fibers have a linear density ranging from 0.15 deniers to 30 deniers; and
    (b) at least one ubiquinone.

24. A composition for topical application on the skin, comprising:
    (a) fibers, wherein said fibers are coated or surface treated; and
    (b) at least one ubiquinone.

25. A composition for topical application on the skin, comprising:
    (a) fibers, wherein said fibers are selected from the group consisting of polyamide fibers, poly-p-phenyleneterephthalamide fibers, cotton fibers, and mixtures thereof; and
    (b) at least one ubiquinone.

26. The composition according to claim 23, wherein said fibers are present in an amount ranging from 1% to 20% by weight, relative to the total weight of the composition.

27. The composition according to claim 23, wherein said ubiquinone is selected from the group consisting of coenzymes Q, alkylubiquinones, and mixtures thereof.

28. The composition according to claim 23, wherein said ubiquinone is coenzyme Q10.

29. The composition according to claim 23, wherein said ubiquinone is present in an amount ranging from 0.01% to 20% by weight, relative to the total weight of the composition.

30. The composition according to claim 23, further comprising a physiologically acceptable medium, wherein said physiologically acceptable medium comprises water.

31. The composition according to claim 23, which is in the form of an emulsion.

32. A method for the treatment of the skin, comprising applying the composition according to claim 23 to the skin, wherein said treatment of the skin is smoothing fine lines, reducing wrinkles, lightening the complexion, lessening pigmentary blemishes, protecting skin from UV radiation, or preventing regreasing of the skin.

33. A method of treatment of the signs of ageing of the skin, comprising applying an effective amount of a composition according to claim 23 to the skin of a subject in need thereof.

34. A method of treating acne or healing a wound to the skin, comprising applying an effective amount of a composition according to claim 23 to the skin of a subject in need thereof.

35. The composition according to claim 24, wherein said fibers are present in an amount ranging from 1% to 20% by weight, relative to the total weight of the composition.

36. The composition according to claim 24, wherein said ubiquinone is selected from the group consisting of coenzymes Q, alkylubiquinones, and mixtures thereof.

37. The composition according to claim 24, wherein said ubiquinone is coenzyme Q10.

38. The composition according to claim 24, wherein said ubiquinone is present in an amount ranging from 0.01% to 20% by weight, relative to the total weight of the composition.

39. The composition according to claim 24, further comprising a physiologically acceptable medium, wherein said physiologically acceptable medium comprises water.

40. The composition according to claim 24, which is in the form of an emulsion.

41. A method for the treatment of the skin, comprising applying the composition according to claim 24 to the skin, wherein said treatment of the skin is smoothing fine lines, reducing wrinkles, lightening the complexion, lessening pigmentary blemishes, protecting skin from UV radiation, or preventing regreasing of the skin.

42. A method of treatment of the signs of ageing of the skin, comprising applying an effective amount of a composition according to claim 24 to the skin of a subject in need thereof.

43. A method of treating acne or healing a wound to the skin, comprising applying an effective amount of a composition according to claim 24 to the skin of a subject in need thereof.

44. The composition according to claim 25, wherein said fibers are present in an amount ranging from 1% to 20% by weight, relative to the total weight of the composition.

45. The composition according to claim 25, wherein said ubiquinone is selected from the group consisting of coenzymes Q, alkylubiquinones, and mixtures thereof.

46. The composition according to claim 25, wherein said ubiquinone is coenzyme Q10.

47. The composition according to claim 25, wherein said ubiquinone is present in an amount ranging from 0.01% to 20% by weight, relative to the total weight of the composition.

48. The composition according to claim 25, further comprising a physiologically acceptable medium, wherein said physiologically acceptable medium comprises water.

49. The composition according to claim 25, which is in the form of an emulsion.

50. A method for the treatment of the skin, comprising applying the composition according to claim 25 to the skin, wherein said treatment of the skin is smoothing fine lines, reducing wrinkles, lightening the complexion, lessening pigmentary blemishes, protecting skin from UV radiation, or preventing regreasing of the skin.

51. A method of treatment of the signs of ageing of the skin, comprising applying an effective amount of a composition according to claim 25 to the skin of a subject in need thereof.

52. A method of treating acne or healing a wound to the skin, comprising applying an effective amount of a composition according to claim 25 to the skin of a subject in need thereof.

53. The composition according to claim 1, wherein said fibers have a length (L) ranging from 0.1 mm to 1 mm.

54. The composition according to claim 23, wherein said fibers have a length (L) ranging from 0.1 mm to 1 mm.

55. The composition according to claim 24, wherein said fibers have a length (L) ranging from 0.1 mm to 1 mm.

56. The composition according to claim 25, wherein said fibers have a length (L) ranging from 0.1 mm to 1 mm.

57. The composition according to claim 1, wherein said fibers have a length (L) ranging from 0.3 mm to 1.5 mm.

58. The composition according to claim 23, wherein said fibers have a length (L) ranging from 0.3 mm to 1.5 mm.

59. The composition according to claim 24, wherein said fibers have a length (L) ranging from 0.3 mm to 1.5 mm.

60. The composition according to claim 25, wherein said fibers have a length (L) ranging from 0.3 mm to 1.5 mm.

* * * * *